United States Patent [19]

Gupta

[11] Patent Number: 4,675,082
[45] Date of Patent: Jun. 23, 1987

[54] RECOVERY OF PROPYLENE GLYCOL MONO T-BUTOXY ETHER

[75] Inventor: Vijai P. Gupta, Berwyn, Pa.

[73] Assignee: Atlantic Richfield Company, Los Angeles, Calif.

[21] Appl. No.: 909,809

[22] Filed: Sep. 22, 1986

[51] Int. Cl.$^4$ .......................... B01D 3/10; C07C 41/42
[52] U.S. Cl. ............................................ 203/74; 203/4; 203/77; 203/81; 203/DIG. 19; 568/678; 568/699
[58] Field of Search ................... 203/74, 77, 81, 4, 99, 203/DIG. 19; 568/678, 699

[56] References Cited

U.S. PATENT DOCUMENTS

| | | | |
|---|---|---|---|
| 1,968,033 | 7/1934 | Evans | 568/678 |
| 2,816,932 | 12/1957 | DiNardo et al. | 568/678 |
| 3,376,203 | 4/1968 | Lackey | 203/4 |
| 3,462,348 | 8/1969 | Wellman et al. | 203/74 |
| 4,144,138 | 3/1979 | Rao et al. | 203/81 |
| 4,340,447 | 7/1982 | Laverick et al. | 203/DIG. 19 |
| 4,544,453 | 10/1985 | Gupta | 568/678 |

Primary Examiner—Wilbur Bascomb
Attorney, Agent, or Firm—Michael S. Jarosz

[57] ABSTRACT

Preparation and recovery of 1-t-butoxy-2-propanol in a high state of purity from a crude etherification reaction product obtained by reaction of isobutylene with propylene glycol in the presence of a solid resin etherification catalyst is disclosed. The crude reaction product is distilled to obtain a 1-t-butoxy-2-propanol-containing distillate, thereby leaving propylene glycol as bottoms; the condensed distillate is then further distilled to separate 1-t-butoxy-2-propanol as an overhead product from higher boiling materials.

12 Claims, 1 Drawing Figure

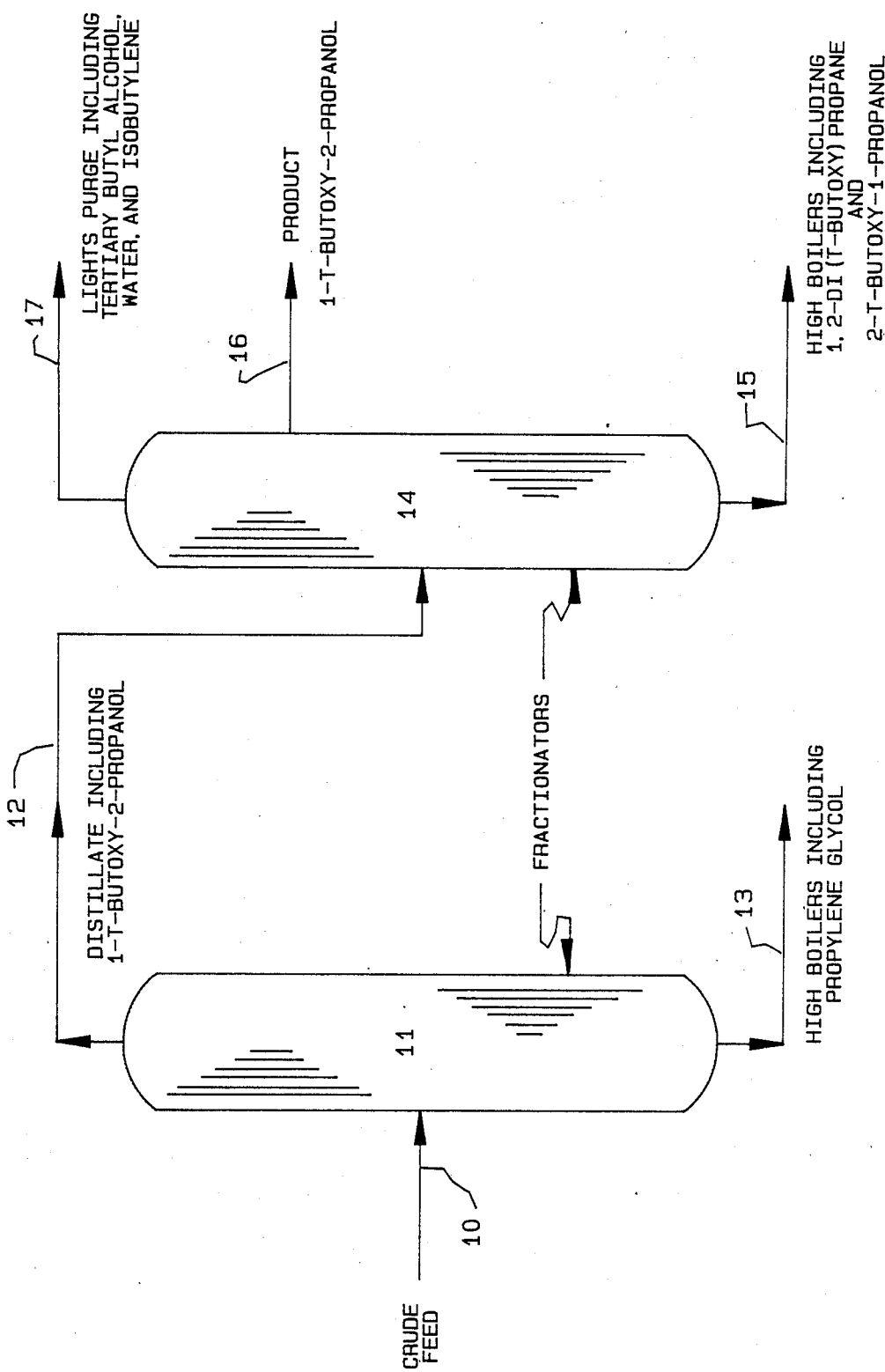

RECOVERY OF PROPYLENE GLYCOL MONO T-BUTOXY ETHER

FIELD OF THE INVENTION

This invention relates to the preparation and recovery of propylene glycol mono t-butoxy ether, i.e. 1-t-butoxy-2-propanol, in a high state of purity.

BACKGROUND OF THE INVENTION

The preparation of ethers, including unsymetrical ethers, by reaction of an olefin with a glycol is well known in the art. The resultant reaction mixture, containing desired glycol ether product, undesired by-products, and unreacted reactants such as glycol, are normally separated in conventional manner by distillation, following removal of catalyst or condensing agent, if employed. In the case of production of 1-t-butoxy-2-propanol, isobutylene is reacted with an excess quantity of propylene glycol in the presence of a solid resin etherification catalyst at appropriate reaction temperatures and pressure to produce a crude reaction product comprised of desired 1-t-butoxy-2-propanol (PTB-1), by-product 2-t-butoxy-1-propanol (PTB-2) unreacted isobutylene and propylene glycol, as well as minor amounts of tertiary butyl alcohol and water. The hydroxyl groups of the glycol ether products produced further react with isobutylene to form the di-ether, 1,2-di(t-butoxy) propane, (DPTB), which is an undesirable by-product. The vapor liquid equilibrium data of the reaction mixture show the following ratio of relative volatilities at 178 mm pressure:

PTB-1/PTB-2 = 1.38

PTB-1/DPTB = 1.54

PTB-2/DPTB = 1.12

However in the actual batch distillation data, it appeared that 1,2-di(t-butoxy) propane was lighter than indicated by the ratio of relative volatilities.

Accordingly, it has been found to be difficult to recover 1-t-butoxy-2-propanol from crude etherification reaction products which exhibit sufficiently low 1,2-di(t-butoxy) propane content to permit commercial use of the desired propylene glycol monotertiary butyl ether in commercial applications, such as in coatings, cleaners, electronic chemicals and inks.

Hence, it is an object of the present invention to provide a process for recovering 1-t-butoxy-2-propanol in a high state of purity without substantial loss while containing minimal amounts of 2-t-butoxy-1-propanol and especially of undesired 1,2-di(t-butoxy) propane from the reaction product obtained by reaction of isobutylene with propylene glycol. Other objects will become apparent to those skilled in the art from the following description.

SUMMARY OF THE INVENTION

Surprisingly, it has been found that the sequence of the fractionation steps involved in recovery of the desired 1-t-butox-2-propanol has a major effect on the final purity of the desired mono-ether obtained, particularly with regard to 1,2-di(t-butoxy) propane content. Substantially improved results are obtained, it has been discovered in accordance with the present invention, when the removal of unreacted propylene glycol precedes the distillation step in which 1-t-butoxy-2-propanol is separated from undesired di(t-butoxy pro-pane and higher boiling materials. Furthermore, this dependence of separation performance upon the sequence of distillation steps is so pronounced that it is of very major economic importance to employ the preferred sequence in order to achieve satisfactory purity at minimum loss of desired 1-t-butoxy-2-propanol. This result is highly unusual and is not in accord with typical vapor liquid equilibria data of the components contained in the crude etherification reaction product.

In accordance with the present invention, there is provided a process for recovering 1-t-butoxy-2-propanol in a high state of purity without substantial loss from the reaction product obtained by the etherification of isobutylene and propylene glycol in the presence of a solid resin etherification catalyst, the crude reaction product containing propylene glycol mono-t-butoxy ethers, undesired 1,2-di(t-butoxy) propane, unreacted propylene glycol and isobutylene and minor amounts of tertiary butyl alcohol and water as well as other high boiling materials. The process includes the sequential steps of: (i) charging the said crude etherification reaction product into a first fractionator, and withdrawing therefrom a first distillation distillate comprising the total reaction product components having a boiling point below that of propylene glycol, thereby leaving as distilland (bottoms) unreacted propylene glycol and components having a boiling point above that of propylene glycol, and (ii) charging the first distillate to a second fractionator and withdrawing therefrom a second distillation distillate overhead or sidestream consisting essentially of desired 1-t-butoxy-2-propanol, thereby leaving as distilland (bottoms) components having a boiling point above that of 1-t-butoxy,-2-propanol, including 2-butoxy-1-propanol and undesired 1,2-di(t-butoxy) propane.

The second distillation overhead generally contains desired 1-t-butoxy-2-propanol in an amount of at least about 98%, the remaining constituents being comprised of minor quantities of 2-t-butoxy-1-propanol and undesired 1,2-di(tbutoxy) propane. Lighter boiling constituents such as isobutylene, tertiary butyl alcohol and water may be purged from the top of the first fractionator, or optionally, may be removed overhead, as purge, in the second fractionator at a distillation temperature below that of 1-t-butoxy2-propanol. Recycling of the bottoms of each of the fractionators to the etherification reactor, it has been found, suppresses the formation of 2-t-butoxy-1-propanol and 1,2-di(t-butoxy) propanol such that once the dynamic equilibrium is reached there is substantially no net make of these components.

DESCRIPTION OF IHE INVENTION

Preparation of 1-t-butoxy-2-propanol may be effected by reaction of isobutylene with propylene glycol in the presence of an solid acid resin catalyst. In general, an excess of propylene glycol is employed, and hence, the mole ratio of propylene glycol to isobutylene will range from about 1.0:1.0 to 5.0:1.0, although ranges from about 1.5:1.0 to 2.5:1.0 are preferred.

Reaction conditions employed to effect the etherification reaction are those conventionally employed in this reaction. Hence, temperatures ranging from between about 25° C. and 200° C., preferably between about 30° C. and 100° C., with accompaning pressures ranging between about 15 and 1,000 psig, preferably between about 10 and 200 psig.

The etherification reaction is effected in the presence of a solid resin etherification catalyst. These catalysts are of relatively high molecular weight carbonatious materials containing at least one sulfonic acid group. Ilustrative solid catalysts employable in this reaction include sulfonated coals such as "Zeo-Karb H" and "Nalcie X" and sulfonated resin type catalysts including reaction products of phenol-formaldehyde resins and surfuric acid such as "Amberlite IR-100" and "Nalcite MX". Preferred resins employable as catalyst in the etherification reacation are cationic exchange resins consisting essentially of sulfonated polystyrene resin, for example, a divinyl benzene cross-linked polystyrene matrix having up to about 25% of copolymerized divinylbenzene contained therein bearing functional nuclear sulfonic acid groups. These resins are manufactured and sold commercially under various trade names, such as "Nalcite HCR" and "Amberlyst 15". Commercial embodiments of such a resin, in general, exhibit a particle size of between about 10 and 50 mesh (U. S. Sieve Series) and may be employed as is, or have a solvent content of up to about 50%, by weight of the composition.

It may be necessary to remove free acidity from the catalyst resin, for example following activation by treatment with a mineral acid, since trace acidity in the effluent causes breakdown of the desired 1-t-butoxy-2-propanol product in subsequant distillation recovery steps. Such removal may readily be effected in conventional manner by passing fresh deionized water through the catalyst bed until the ph of the effluent water stabilizes at above about 5 pH. Any water remaining in the bed following draining, will be converted to tertiary butyl alcohol during the initial stage of the reaction and is removed as lights in the distillation recovery scheme.

The reaction may be effected in either a stirred slurry batch reactor or in a fixed bed continuous flow reactor. In general, in a stirred reactor, catalyst concentration may range from between about 0.5% to 20% (dry basis) by weight of the reaction contents, and from 2% to 10% being preferred range, it being understood that no criticality is attached to catalyst concentration and that any catalyst concentration sufficient to provide the desired catalytic effect are employable. The reaction time may vary widely and in general, will range from about 1 to about 20 hours, preferably from about 1 to about 5 hours.

The 1-t-butoxy-2-propanol product recovered as said second distillation overhead is of at least 98% purity, normally at least about 99.0% purity, and generally contains not more than about 1% of 2-t-butoxy-1-propanol, not more than about 0.5% of 1,2-di(t-butoxy) propane, not more than about 0.1% of propylene glycol, and not more than about 0.1% of isobutylene.

SPECIFIC EMBODIMENT OF THE INVENTION

The present invention is now described with reference to FIG. 1 of the accompanying drawing which illustrates one embodiment of the recovery process of the invention.

A crude 1-t-butoxy-2-propanol containing product which serves as feed for the process of the patent invention may be obtained by liquid phase reaction of isobutylene and propylene glycol catalyzed by an acidic ion exchange resin catalyst, typically Amberlyst-15 ion exchange resin, in a fixed bed while employing external circulation of feed reactants from a batch tank through the bed. Isobutylene is injected into the circulating stream ahead of the fixed bed inlet. The reaction, effected at a temperature of about 50° C. and a pressure of about 50 psig, is completed in about seventeen hours; if desired, unreacted isobutylene may be vented to safe disposal. The crude reaction product containing substantial quantities of propylene glycol, generally from about 10 to about 75 percent, by weight, thereof, may then be pumped to storage or may be subjected directly to the process of the invention for final recovery of substantially pure 1-t-butoxy-2-propanol product.

Recovery of the desired 1-t-butoxy-2-propanol from the crude reaction product is accomplished in a two-step fractionation, which may be effected either batch or in continuous manner. Hence, the crude 1-t-butoxy-2-propanol reaction product obtained from the described etherification reaction is charged through Line 10 to a distillation zone of first Fractionator 11. Depending upon the etherification reaction conditions employed, the crude reaction product generally conforms to a composition of the following character:

| Component | Percent by Weight |
|---|---|
| 1-t-butoxy-2-propanol | 40 to 70 |
| 2-t-butoxy-1-propanol | 2 to 10 |
| propylene glycol | 10 to 75 |
| isobutylene | 0.05 to 5.0 |
| 1,2-di(t-butoxy) propane | 1 to 10 |
| tertiary butyl alcohol | 0.05 to 5.0 |
| water | trace to 1.0 |

Fractionator 11 is operated at conditions such that a propylene glycol free side stream, i.e. a distillate containing less than about 0.1% propylene glycol, is obtained illustratively, when carried out on a continuous basis in a 20 theoretical stage column at 200 milimeter overhead pressure with a 3/1 reflux ratio. Hence, substantially, all higher boiling materials including propylene glycol are removed in a first liquid bottoms product through Line 13. Fractionator 11 is generally operated at a pressure of from about 1 to 20 pounds per square inch absolute (psia) and at an overhead temperature of from about 50° C. to about 175° C., preferably of from about 75° C. to about 140° C. It is particularly advantageous to operate Fractionator 11 such that the top zone thereof is at a pressure of between about 8 and 12 psia. Fractionator 11 generally contains from about 10 to 40 theoretical vapor-liquid contacting stages.

The distilland bottoms from Fractionator 11 comprised substantially of high boiling components including substantially all of the unreacted propylene glycol, may be employed to make up subsequent reaction charge together with fresh propylene glycol feed.

The distillate evolved from Fractionator 11 is taken to intermediate storage as feed to be charged to a second stage distillation, for example, as illustrated by Fractionator 14, or may be subjected directly to such distillation operation. The distillate obtained from Fractionator 11, in addition to containing desired 1-t-butoxy-2-propanol, will also contain up to about 5% of isobutylene, up to about 10% of 2-t-butoxy-1-propanol, up to about 10% of 1,2-di(t-butoxy) propane and small amounts of tertiary butyl alcohol and other light impurities. If desired, lights impurities may be purged prior to subjection of the distillate from Fractionator 11 into the second Fractionator 14. Illustratively, the second distillation column, Fractionator 14, will be operated once sufficient distillate from the first column is in storage. In general, Fractionator 14 is operated advantageously at a pressure of from about 1 to about 15 psia and at an overhead (top) zone temperature of from about 60° C. to about 170° C. and preferably from about 75° C. to about 125° C. Particularly preferred operation involves a pressure of about 200 milimeters overhead and a 10/1 reflux ratio. From about 10 to about 40 theoretical vapor-liquid contacting stages, illustratively 30 theoretical ages are included in Fractionator 14.

Alternatively, a lights purge for removal of isobutylene and other lights materials such as tertiary butyl alcohol and water, may be included as a part of Fractionator 14 and may be removed as overhead through Line 17, as illustrated in FIG. 1. Desired product, 1-t-butoxy-2-propanol is recovered as a distillation overhead through Line 15. This second fractionator distillation overhead contains of least about 98%, and generally of at least 99.0% purity of desired 1-t-butox-2-propanol product, together with minor amounts of 2-t-butoxy-1-propanol, and less than about 0.5% of 1,2-di(t-butoxy) propane. High boiling components i.e. materials boiling above boiling point of 1-t-butoxy-2-propanol are removed as a second liquid bottoms through Line 15; these components include undesired 1,2-di(t-butoxy) propane as well as 2-t-butoxy-1-propanol. The bottoms from both Fractionator 11 and Fractionator 14 may be recycled to the reaction etherification step to suppress formation of undesired 1,2-di(t-butoxy) propane and 2-t-butoxy-1-propanol.

As is indicated in Table I, below, the vapor liquid equilibrium ratio for the system subjected to the recovery process of the present invention is complex.

TABLE I

| °C./mm Hg | Component | Wt. % Vapor | Wt. % Liquid |
|---|---|---|---|
| Composition A | | | |
| 106.7/178 | PTB-1 | 87.12 | 82.9 |
| | PTB-2 | 5.12 | 6.69 |
| | PDTB | 7.13 | 10.4 |
| Composition B | | | |
| 127.8/295.5 | PTB-1 | 73.2 | 53.3 |
| | PTB-2 | 3.77 | 3.94 |
| | Propylene Glycol | 11.6 | 34.1 |
| | PDTB | 11.5 | 6.63 |

In the presence of propylene glycol, the 1,2-di(t-butoxy) propane becomes the lightest component as is evidenced from Table 1; in contradistinction, in the absence of propylene glycol, as evidenced from Table 1 above, undesired 1,2-di(t-butoxy) propane becomes heavier than desired 1-t-butoxy-2-propanol product and is nearly inseparable from impurity 2-t-butoxy-1-propanol. Since propylene glycol itself is the heaviest component obtained in the reaction mixture evolving from the etherification reaction, volatility inversion between 1-t-butoxy-2-propanol and 1,2-di(t-butoxy) propane occurs in the tower between the top (propylene glycol free) and the bottom (propylene glycol rich) sections. The recovery scheme of the present invention, therefore, requires effecting two stages of fractionation in sequence.

The process of the present invention is illustrated further by the following typical example with reference to the drawing.

EXAMPLE 1

A crude 1-t-butoxy-2-propanol product, 100 parts by weight, obtained from the etherification of propylene glycol with isobutylene in the presence of an Amberlist 15 ion exchange resin catalyst, of the following composition was charged from line 10 to Fractionator 11:

| Component | %/Wt |
|---|---|
| isobutylene | 0.8 |
| propylene glycol | 41.5 |
| tertiary butyl alcohol | 1.0 |
| water | Trace |
| 1,2-di(butoxy) propane | 3.8 |
| 2-t-butoxy-1-propanol | 4.3 |
| 1-t-butoxy-2-propanol | 48.3 |

Overhead taken from Fractionator 11 through Line 12 comprised about 87 percent by weight of desired 1-t-butoxy-2-propanol. Bottoms product removed from Line 13 comprised about 8.4 percent by weight of propylene glycol. Fractionator 11 contained 30 trays and was operated at 10 psia at an overhead temperature of 121° C. with a reflux feed ratio of 1.

The overhead product taken from Fractionator 11 was charged directly to Fractionator 14. Lights purged from Fractionator 14 comprised minor quantities of isobutylene, tertiary butyl alcohol and water. The intermediate product taken from Fractionator 14 through Line 15 comprised 99.2 percent, by weight, of desired 1-t-butoxy-2-propanol 0.2 percent, by weight, of 2-t-butoxy-1-propanol, and 0.1 percent, by weight, 1,2-di-(t-butoxy) propane. Bottoms product removed from Fractionator 14 through Line 15 comprised 75.3 percent, by weight, of undesired 1,2-di (t-butoxy) propane, 18.2 percent, by weight, of 2-t-butoxy-1-propanol and 6.2 percent by weight of propylene glycol. Fractionator 14 contained 30 trays and was operated at 10 psia at a product withdrawl zone temperature of about 120° C. with a reflux feed ratio of 1.

As indicated, therefore, the present invention provides a novel process for the recovery 1-t-butoxy-2-propanol of a high degree of purity with a minimal losses based upon the crude feed charged to Fractionator 11.

I claim:

1. A process for the recovery of 1-t-butoxy-2-propanol in a high state of purity from a cruce reaction product obtained by etherification of propylene glycol with isobutylene, said reaction product containing substantial quantities of unreacted propylene glycol, said process comprising the sequential steps of:
   (a) charging the crude reaction product mixture into a first fractionator, withdrawing therefrom a first distillation overhead comprising essentially 1-t-butoxy-2-propanol and components having a lower boiling point than that of propylene glycol, and withdrawing therefrom a first distillation bottoms containing propylene glycol and material having a higher boiling point than that of 1-t-butoxy-2-propanol, followed by
   (b) charging the said first distillation overhead to a second fractionator, withdrawing therefrom a second distillation overhead containing 1-t-butoxy-2-propanol substantially free of higher boiling materials, and withdrawing therefrom a second distillation bottoms containing higher boiling materials.

2. The process of claim 1 wherein materials having a lower boiling point than that of 1-t-butoxy-2-propanol are purged prior to its recovery in said second fractionator.

3. The process of claim 2 wherein said first fractionator is operated at a top zone temperature of from about 50° C. to about 175° C.

4. The process of claim 3 wherein said second fractionator is operated at a top zone temperature of from about 60° C. to about 170° C.

5. The process of claim 4 wherein said second fractionator is operated at a top zone temperature of from about 75° C. to about 125° C.

6. The process of claim 2 wherein said first fractionator is operated at a pressure of from between about 1 and about 15 psia.

7. The process of claim 5 wherein said second fractionator is operated at a pressure of from about 8 to about 12 psia.

8. The process of claim 2 wherein materials having a boiling point lower than 1-t-butoxy-2-propanol are purged from the first fractionator.

9. The process of claim 2 wherein the 1-t-butoxy-2-propanol product obtained is of at least 98% purity and contains less than about 0.5 percent, by weight, of 1,2-di (t-butoxy) propane.

10. The process of claim 2 wherein said etherification and distillation recovery processes are effected in a continuous manner.

11. The process of claim 10 wherein said first and second distillation bottoms are recycled to the etherification reaction.

12. The process of claim 11 wherein the 1-t-butoxy-2-propanol product obtained is of at least 99.5% purity and contains less than about 0.1 percent, by weight, of 1,2-di (t-butoxy) propane.

* * * * *